(12) United States Patent
Patnaikuni et al.

(10) Patent No.: US 11,301,041 B1
(45) Date of Patent: Apr. 12, 2022

(54) HAND TREMOR ACCESSIBLE USING AUGMENTED REALITY USER INTERFACE

(71) Applicant: International Business Machines Corporation, Armonk, NY (US)

(72) Inventors: Subha Kiran Patnaikuni, Visakhapatnam (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 17/039,077

(22) Filed: Sep. 30, 2020

(51) Int. Cl.
*A61B 90/00* (2016.01)
*G16H 30/20* (2018.01)
*G06F 3/01* (2006.01)
*G06T 19/00* (2011.01)
*A61B 5/11* (2006.01)

(52) U.S. Cl.
CPC ............ *G06F 3/014* (2013.01); *A61B 5/1101* (2013.01); *G06F 3/017* (2013.01); *G06T 19/006* (2013.01)

(58) Field of Classification Search
CPC .................................................. A61B 5/1101
USPC ........................................................ 345/633
See application file for complete search history.

(56) References Cited

U.S. PATENT DOCUMENTS

| 10,078,954 B1 * | 9/2018 | Tate | .................... G06K 9/00335 |
| 2013/0303837 A1 * | 11/2013 | Berka | .................... A61B 5/369 600/28 |
| 2014/0055352 A1 * | 2/2014 | Davis | .................... G06F 3/0304 345/156 |
| 2014/0109017 A1 * | 4/2014 | Benko | .................... G06F 3/0488 715/858 |
| 2014/0204036 A1 | 7/2014 | Schillings | |
| 2019/0004604 A1 | 1/2019 | Wang | |
| 2019/0180473 A1 | 6/2019 | Guleryuz | |
| 2020/0026352 A1 | 1/2020 | Wang | |
| 2020/0312453 A1 * | 10/2020 | Raisanen | .............. G16H 10/60 |
| 2020/0353239 A1 * | 11/2020 | Daniels | .................. A61B 5/296 |
| 2020/0372714 A1 * | 11/2020 | Soryal | .................... G16H 30/20 |

(Continued)

FOREIGN PATENT DOCUMENTS

CN 108958590 A 12/2018

OTHER PUBLICATIONS

"Stabilizing Graphically Extended Hand for Hand Tremors", Kai Wang et al., IEEE 2018.*

(Continued)

*Primary Examiner* — Javid A Amini
(74) *Attorney, Agent, or Firm* — Andrew Aubert

(57) ABSTRACT

Disclosed are techniques for modifying Augmented Reality (AR) device user interfaces to improve accessibility for individuals with tremors in their hands and/or fingers. A historical data set of finger movements is generated using circuitry printed onto fingernails of an individual. The historical data set is used to determine patterns for tremors in the fingers and hands of the individual. These patterns are then used to modify interactive elements of a user interface displayed by an AR device operated by the individual according to their individual pattern. Modifications to the interactive elements include modifying depth of the interactive elements to prevent unintended activation of the interactive elements through gesture-based controls resulting from the tremors.

20 Claims, 6 Drawing Sheets

(56) References Cited

U.S. PATENT DOCUMENTS

2021/0068674 A1* 3/2021 Erivantcev ............. A61B 5/742

OTHER PUBLICATIONS

"Parkinson's disease", Mayo Clinic, Last printed Sep. 30, 2020, 5 pages, <https://www.mayoclinic.org/diseases-conditions/parkinsons-disease/symptoms-causes/syc-20376055>.

Buchmann, et al., "FingARtips—Gesture Based Direct Manipulation in Augmented Reality", GRAPHITE '04: Proceedings of the 2nd international conference on Computer graphics and interactive techniques in Australasia and South East Asia, Jun. 2004, pp. 212-221, <https://dl.acm.org/doi/10.1145/988834.988871>.

Sakuma, et al., "Wearable Nail Deformation Sensing for Behavioral and Biomechanical Monitoring and Human-Computer Interaction", Scientific Reports, (2018) 8:18031, 11 pages.

Unknown, "Shaking hands (hand tremors): 14 causes and treatments," https://www.medicalnewstoday.com/articles/322195#causes, printed Sep. 30, 2020, 3 pgs.

* cited by examiner

HAND TREMOR ACCESSIBLE USING AUGMENTED REALITY USER INTERFACE

BACKGROUND

The present invention relates generally to the field of augmented reality user interfaces, and more particularly to accessibility improvements to augmented reality user interfaces for individuals with hand tremors.

Augmented reality (AR) systems refer to interactive experiences with a real-world environment where objects which reside in the real world are modified by computer-generated perceptual information, sometimes across two or more sensory modalities, including visual, auditory, haptic, somatosensory and olfactory. AR systems are frequently defined to require three basic features: a combination of real and virtual worlds, real-time interaction, and accurate 3D registration of virtual and real objects. The overlaid sensory information typically comes in two varieties. The first variety is constructive (i.e. additive to the natural environment), and the second variety is destructive (i.e. masking of the natural environment). This experience is smoothly interwoven with the physical world in such a way that it is frequently perceived as an immersive aspect of the real environment. In this way, AR alters a person's ongoing perception of a real-world environment, as contrasted to virtual reality which fully replaces the user's real-world environment with a simulated one. AR is related to two terms which are largely synonymous: mixed reality and computer-mediated reality. With the help of advanced AR technologies (e.g. incorporating computer vision, leveraging AR cameras into smartphone applications and object recognition) information about the surrounding real world of the AR user becomes interactive and digitally manipulated. Information about the environment and objects within it is overlaid onto the real world. User interfaces (UI) of AR devices often include projecting digital content and interactive elements into the field of view of the user. The user interacts with the digital content and interactive elements through speech recognition systems that convert a user's spoken words into computer instructions, gesture recognition systems that translate a user's body movements through either visual detection via cameras or from sensors embedded in a peripheral device such as a wand, stylus, pointer, glove or other body wear.

A tremor is an involuntary and somewhat rhythmic muscle contraction and relaxation involving twitching movements or oscillations of one or several body parts. Tremors, the most common involuntary movement, can affect the hands, arms, eyes, face, head, vocal folds, trunk, and legs. Most tremors present in the hands. In some people, a tremor is a symptom of another underlying neurological disorder such as Parkinson's disease.

SUMMARY

According to an aspect of the present invention, there is a method, computer program product and/or system for use with an augmented reality (AR) device that performs the following operations (not necessarily in the following order): (i) receiving a historical hand tremor data set corresponding to a user; (ii) determining a hand tremor pattern based, at least in part, on the historical hand tremor data set; (iii) displaying an augmented reality user interface on the AR device worn by the user; (iv) determining a potential user interface interaction between at least one hand of the user and the augmented reality user interface; and (v) modifying the augmented reality user interface based, at least in part, on the hand tremor pattern.

DETAILED DESCRIPTION

Figure 1:
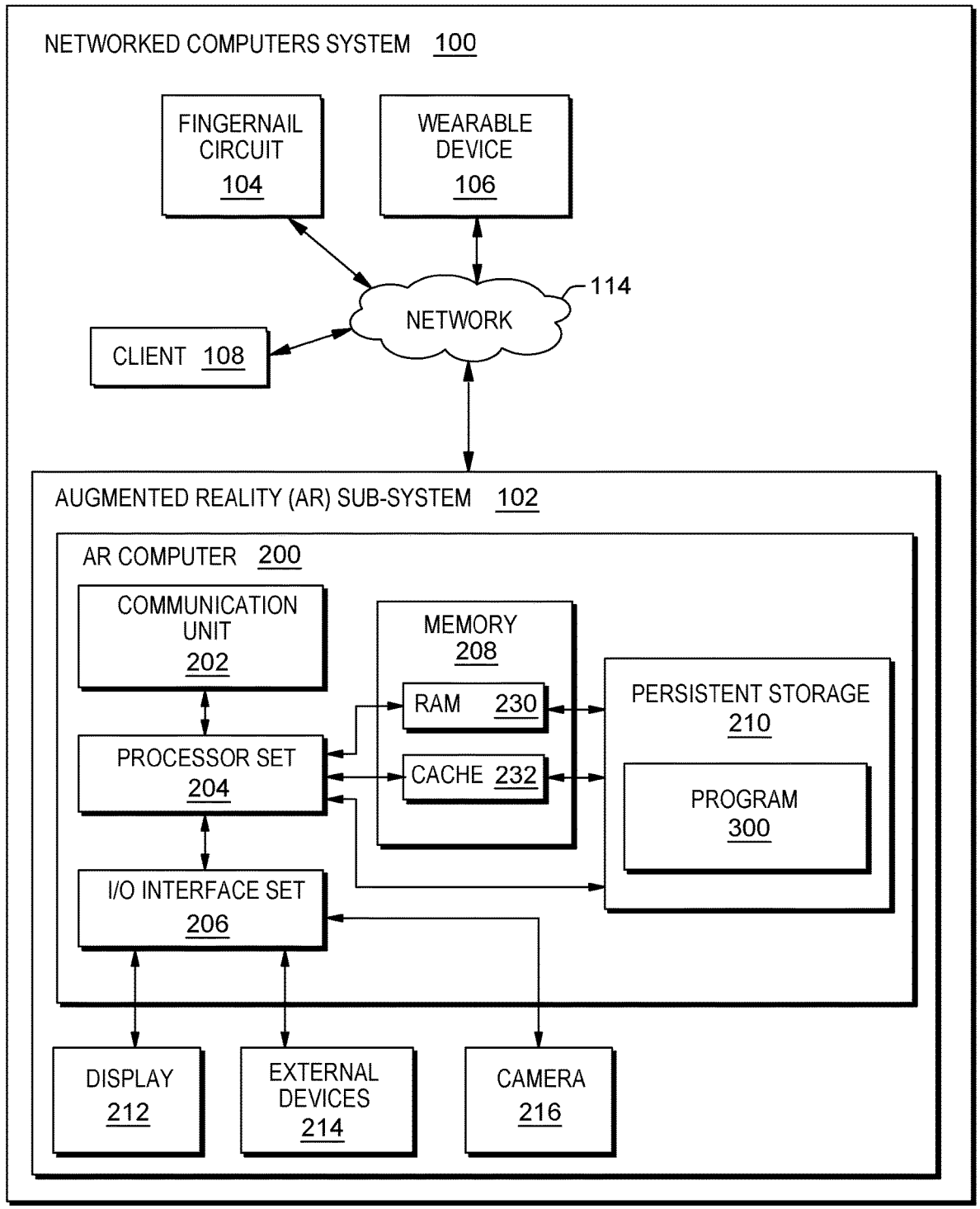
FIG. 1 is a block diagram view of a first embodiment of a system according to the present invention.

Some embodiments of the present invention are directed to techniques for modifying Augmented Reality (AR) device user interfaces to improve accessibility for individuals with tremors in their hands and/or fingers. A historical data set of finger movements is generated using circuitry printed onto fingernails of an individual. The historical data set is used to determine patterns for tremors in the fingers and hands of the individual. These patterns are then used to modify interactive elements of a user interface displayed by an AR device operated by the individual according to their individual pattern. Modifications to the interactive elements include modifying depth of the interactive elements to prevent unintended activation of the interactive elements through gesture-based controls resulting from the tremors.

This Detailed Description section is divided into the following subsections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium, also referred to as machine readable storage device, can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be anything made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in FIG. 1, networked computers system 100 is an embodiment of a hardware and software environment for use with various embodiments of the present invention.

Networked computers system 100 includes: server subsystem 102 (sometimes herein referred to, more simply, as subsystem 102); fingernail circuit 104; wearable device 106; client 108; and communication network 114. Server subsystem 102 includes: server computer 200; communication unit 202; processor set 204; input/output (I/O) interface set 206; memory 208; persistent storage 210; display 212; external device(s) 214; camera 216; random access memory (RAM) 230; cache 232; and program 300.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen. Camera 216 is a video camera module that records optical information that is stored in memory 208 and/or persistent storage 210.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

State of the art technology exists for printing a circuit onto a human fingernail, with a circuit including: (a) a three dimensional accelerometer for accurately measuring 3-d movements of individual fingers; and (b) a wireless transmitter for communicating digital information over a wireless electronic communication network (for example, wi-fi, Bluetooth, NFC).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
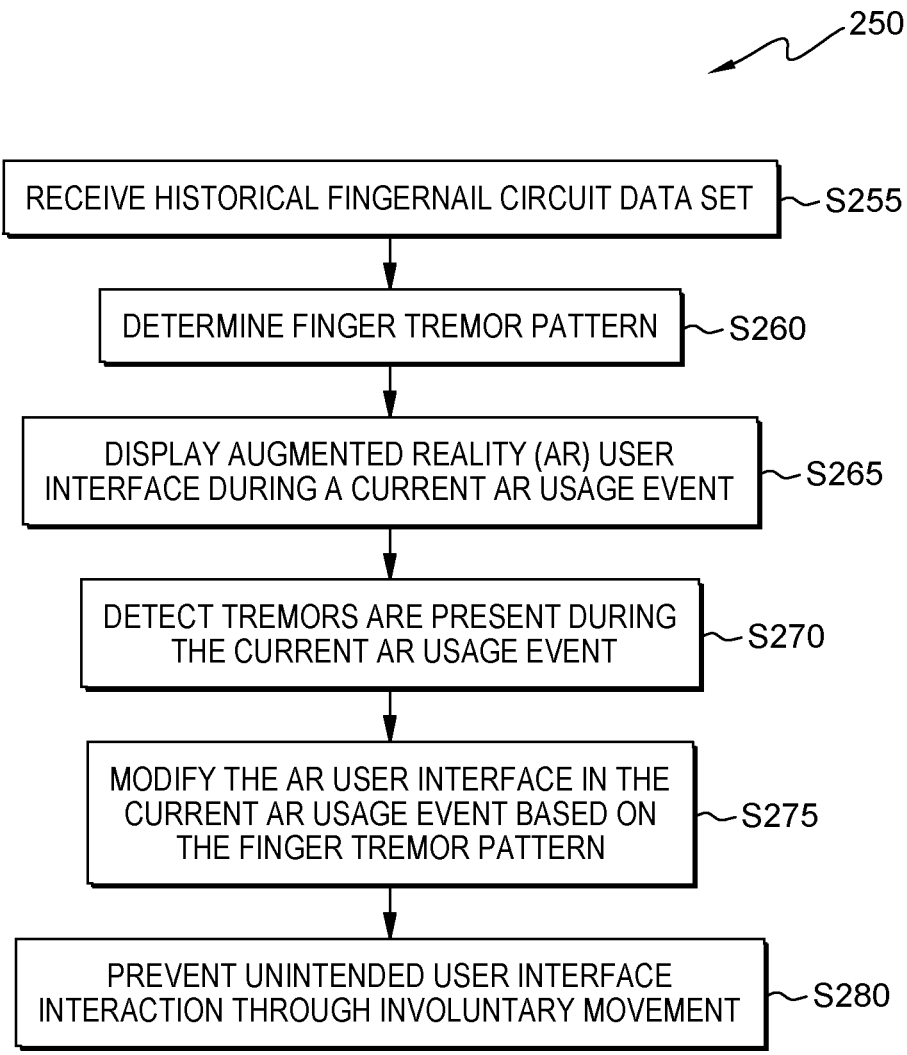
FIG. 2 is a flowchart showing a first embodiment method performed, at least in part, by the first embodiment system.
Figure 3:
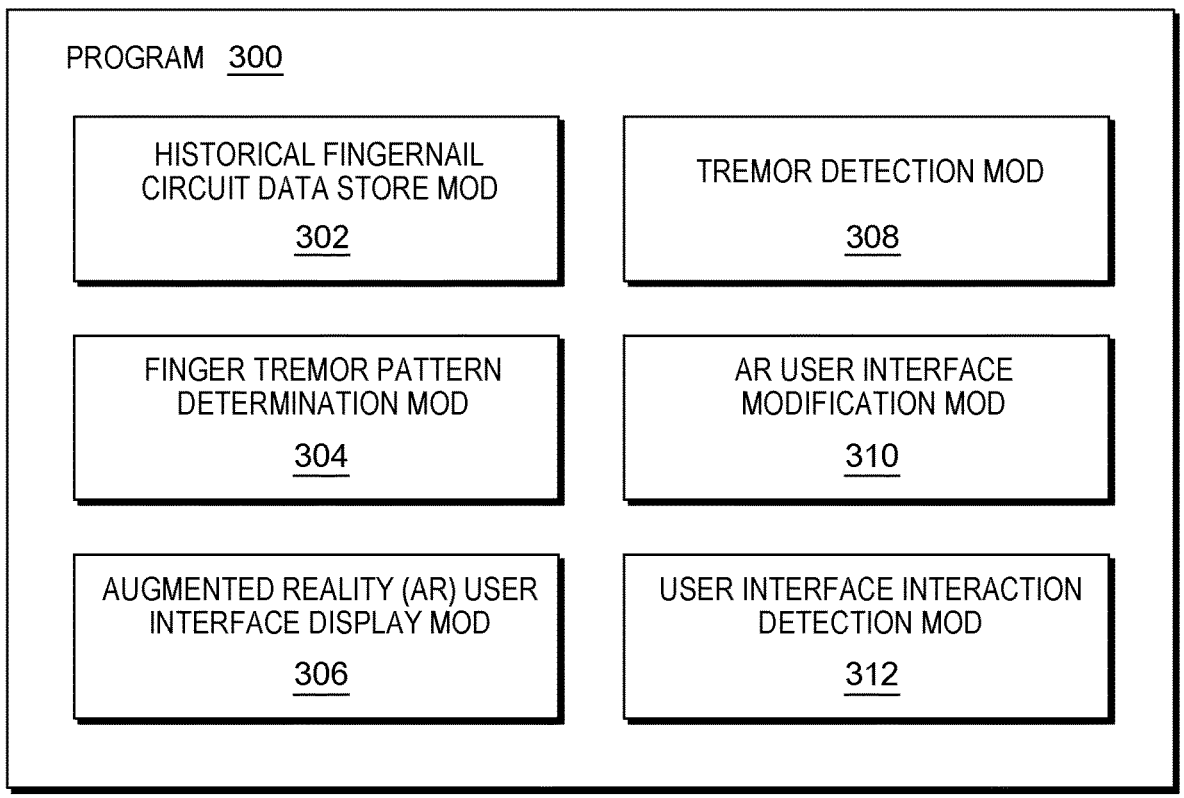
FIG. 3 is a block diagram showing a machine logic (for example, software) portion of the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or control performance of at least some of the method operations of flowchart 250. This method and associated software will now be discussed, over the course of the following paragraphs, with extensive reference to the blocks of FIGS. 1, 2, 3, and screenshots of FIGS. 4A-4B, 5A-5B, 6A-6B and 7A-7B.

Processing begins at operation S255, where historical fingernail circuit data store module ("mod") 302 receives a historical fingernail circuit data set. In this simplified embodiment, Patient A is afflicted with essential tremor, affecting each of the fingers and thumbs of both of their hands. A fingernail circuit, shown as fingernail circuit 104 of FIG. 1, includes a 3-d accelerometer and wireless transmitter, was printed onto each digit of both of the hands of Patient A and worn for 24 hours, recording a historical fingernail circuit data set. The historical fingernail circuit data set includes 24 hours of 3-d positional data for each individual digit, separated into data subsets for each finger. In some alternative embodiments, the fingernail circuits are printed on fewer than all 10 digits (for example, just one index finger, or both index fingers). Patient A is also wearing wearable device 106, a smartwatch with an integrated 3-d accelerometer, to measure and record position data for the wrist of their right arm. This positional data for the wrist can help isolate finger and hand movements from overall body or arm movements. The historical fingernail circuit data set is received over network 114 by AR sub-system 102, an AR device in an eye-glasses type form factor. In alternative embodiments, the historical fingernail circuit data set includes positional data over different lengths of time (for example, one hour, one week, one month, or one year). In alternative embodiments, other types of AR devices are used, such as a head mounted display (HMD), heads up display, contact lens display, virtual retinal display (VRD), or an EyeTap device.

Processing proceeds to operation S260, where finger tremor pattern determination mod 304 determines a finger tremor pattern. In this simplified embodiment, the finger tremor pattern includes average frequency and amplitude values for each finger in each of three dimensions corresponding to horizontal, vertical, and depth relative to the wrist of Patient A. These values are determined using the individual finger 3-d positional data from the fingernail circuits and the wrist positional data from wearable device 106. In some alternative embodiments, the finger tremor pattern includes separate context-based patterns. For example, separate patterns are determined depending on the type of activity that the user (such as Patient A) is engaged in when the 3-d positional data for each finger is recorded, or separate patterns for different segments of a timespan (different patterns for morning or night, or based on hours from the last sleep cycle of the user).

Processing proceeds to operation S265, where Augmented Reality (AR) user interface display mod 306 displays an AR user interface during a current AR usage event. In this simplified embodiment, Patient A is wearing AR sub-system 102, an eye-glasses form factor augmented reality device. Display 212 of FIG. 1, a component of AR sub-system 102, projects digital content of a user interface onto a transparent surface in front of the eyes of Patient A at varying perceived depths or distances from the perspective of Patient A. Some examples of this are shown in screenshots 600A and 700A of FIGS. 6A and 7A, respectively, which will be discussed in greater detail below.

Processing proceeds to operation S270, where tremor detection mod 308 detects tremors are present during the current AR usage event. In this simplified embodiment, Patient A no longer has fingernail circuits on their digits. Patient A is also initiating a usage event of AR sub-system 102 by wearing sub-system 102 on their head and turning sub-system 102 on, where digital content of a user interface is displayed on display 212. Tremor detection mod 308 detects tremors by analyzing video recorded by camera 216 of FIG. 1 when Patient A brings their hands into view of camera 216, which is directed towards the view space of Patient A, where AR sub-system 102 projects the digital content of the user interface. When Patient A brings their hands into view to interact with the digital content of the user interface, camera 216 observes the motion of their hands. As Patient A's index finger on their right hand tremors while observed by camera 216, tremor detection mod 308 detects these tremors by analyzing movement of the right index finger on a frame to frame basis and using state of the art computer vision techniques for determining distance from a camera to an object observed by the camera to define a scale for estimating the movement of the observed index finger, and comparing the estimated movement of the observed index finger to the finger tremor pattern. The estimated movement is sub-classified into the three dimensions: horizontal movement, vertical movement, and depth. These dimensions are oriented to a coordinate system based on camera 216, with depth corresponding to distance from camera 216 and horizontal/vertical movement corresponding to side to side or up and down movement from the perspective of camera 216. Note that camera 216 has a similar viewing angle and perspective of a human wearing AR sub-system 102, so tremor detection mod 308 additionally determines the location of the wrist of Patient A in the camera feed of camera 216 and transforms the estimated movement from the perspective of the appropriate wrist of Patient A.

Figure 4A:
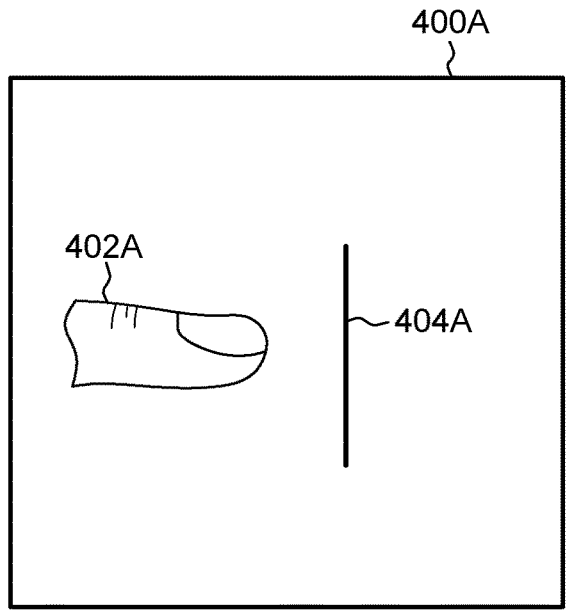
FIG. 4A is a screenshot view generated by the first embodiment system.
Figure 4B:
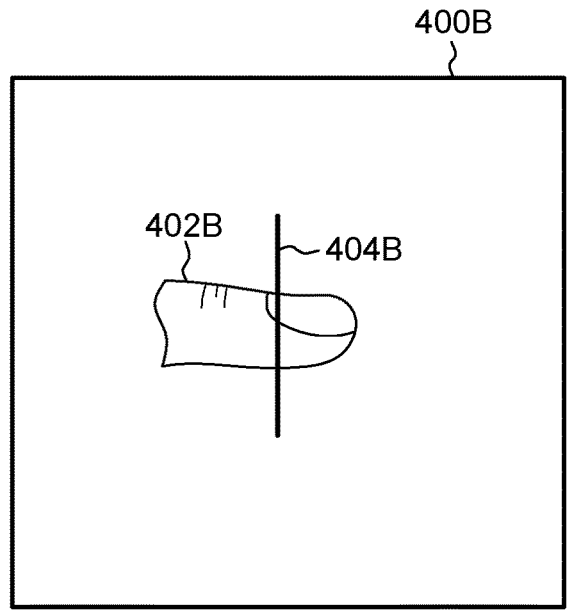
FIG. 4B is a screenshot view generated by the first embodiment system.
Figure 5A:
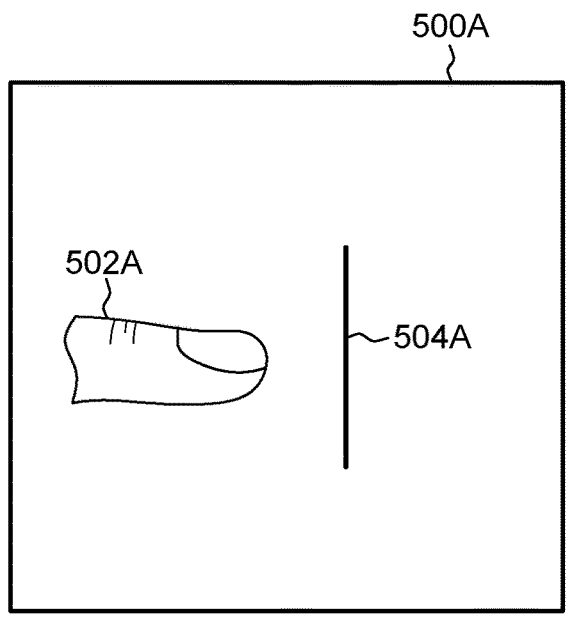
FIG. 5A is a screenshot view generated by the first embodiment system.
Figure 5B:
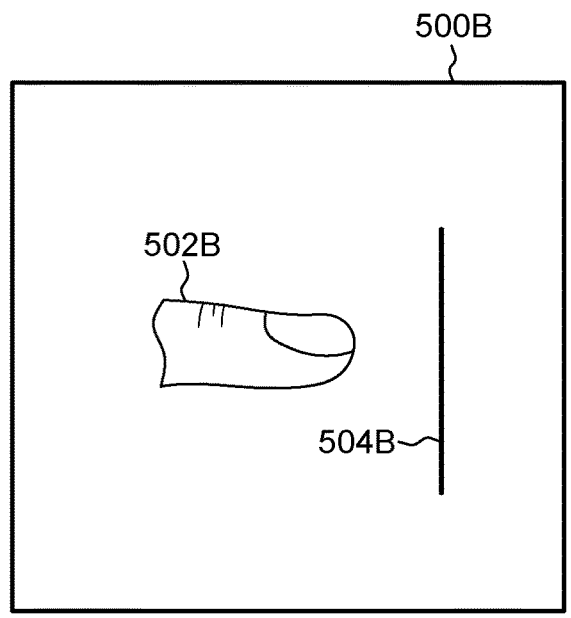
FIG. 5B is a screenshot view generated by the first embodiment system.
Figure 6A:
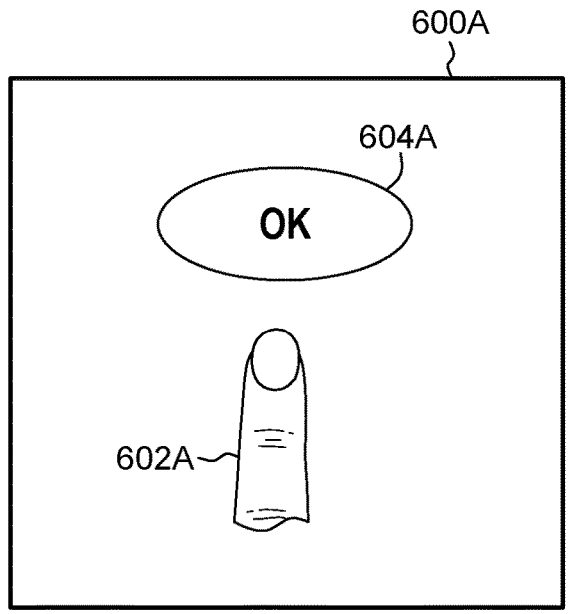
FIG. 6A is a screenshot view generated by the first embodiment system.
Figure 6B:
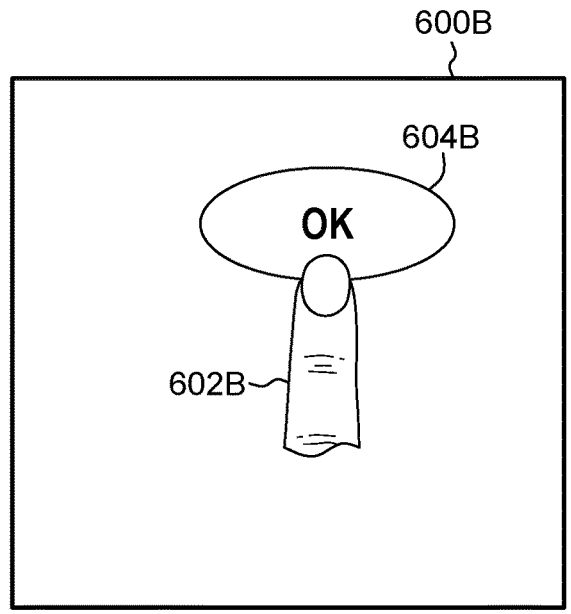
FIG. 6B is a screenshot view generated by the first embodiment system.
Figure 7A:
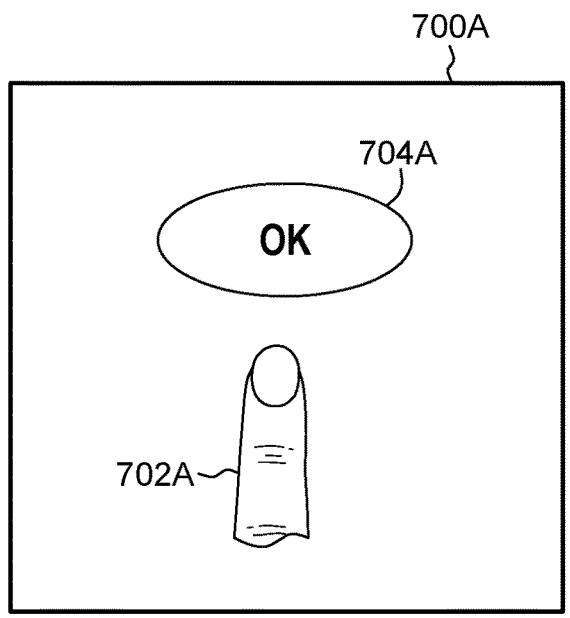
FIG. 7A is a screenshot view generated by the first embodiment system.
Figure 7B:
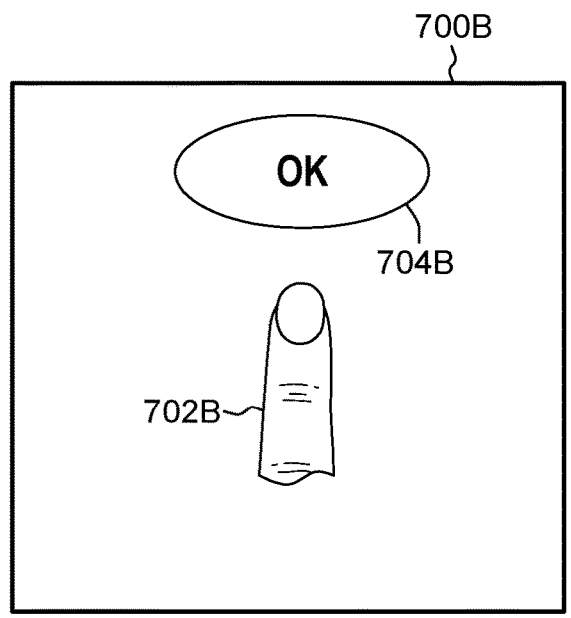
FIG. 7B is a screenshot view generated by the first embodiment system.

An example is shown in screenshot 600A of FIG. 6A and screenshot 700A of FIG. 7A, which respectively include finger 602A/702A and digital content 604A/704A, an interactive user interface element as it appears from the perspective of Patient A. The outstretched index finger of Patient A, shown as finger 602A/702A appears proximate to digital content 604A/704A, which is projected onto display 212 to appear at an appropriate depth from Patient A, despite display 212 being relatively proximate to the eyes of Patient A. FIGS. 4A and 5A also show the same, including finger 402A/502A and digital content 404A/504A, respectively, from the perspective of a hypothetical observer viewing the same from a perpendicular viewpoint so as to better illustrate depth in the context of the present invention and will be discussed in greater detail below.

When the estimated movement of the right index finger exceeds a threshold based on the finger tremor pattern, the estimated movement is determined to be an intentional movement. When the estimated movement meets or falls below the threshold, it is determined to be an involuntary tremor. These comparisons can be done based on each of the sub-classes of the estimated movement. In this simplified embodiment, the threshold is 25% of the average amplitude values determined in the finger tremor pattern. In some alternative embodiments, other techniques are used to detect tremors during the current AR usage event, such as determining if a tremor is present by identifying any oscillating movement of Patient A's digits or hands observed by camera 216, and comparing if the frequency of the oscillating movement matches, within a threshold, the average frequencies determined in the finger tremor pattern.

Processing proceeds to operation S275, where AR user interface modification mod 310 modifies the AR user interface in the current AR usage event based on the finger tremor pattern. In this simplified embodiment, AR user interface modification mod 310 modifies the AR user interface by adjusting or modifying the perceived depth of digital content of the user interface displayed on display 212 according to the average amplitude for depth determined in the finger tremor pattern, oscillating the perceived depth of the digital content synchronized to tremors observed by camera 216. This is shown in screenshot 500B of FIG. 5B and screenshot 700B of FIG. 7B, where finger 502B/702B, respectively, has extended through space previously perceived as occupied by digital content 504B/704B, respectively. Digital content 504B/704B is perceived at a deeper/further depth, at a relative distance from the right index finger of Patient A if no tremor was present causing the right index finger of Patient A to extend towards and retract from the digital content as perceived by Patient A.

Processing proceeds to operation S280, where user interface interaction detection mod 312 prevents an unintended user interface interaction through involuntary movement. In this simplified embodiment, the digital content of the user interface displayed on display 212 is an interactive element in the form of an "OK" button, as shown in digital content 604A/604B/704A/704B of screenshots 600A/600B/700A/700B of FIGS. 6A/6B/7A/7B, respectively. On display 212, digital content is displayed at varying depths and varying horizontal/vertical positions. When camera 216 observes a hand or digit of Patient A enter the depth and horizontal/vertical position of digital content that is interactive, an interaction event is triggered. In this simplified embodiment, an interaction event would result if the right index finger of Patient A through an involuntary tremor in their right index finger, entered the depth and horizontal/vertical position of digital content 404B/604B, shown in FIGS. 4B/6B, respectively. This would result in an unintended user interface interaction through involuntary movement. However, because AR user interface modification mod 310 modified the AR user interface in the current AR usage event to extend the depth of the digital content, screenshots 500B and 700B of FIGS. 5B and 7B respectively illustrate the results, where digital content 504B/704B are adjusted or modified to be perceived at a further depth based on the finger tremor pattern, preventing an unintended user interface interaction through involuntary movement, and providing a more accessible interface for AR devices for those afflicted by tremors in their hands and/or fingers. Another way to describe this is that user interface interaction detection mod 312 filters hand and/or finger movements corresponding to the tremor and adjusts or modifies digital content of the user interface accordingly to prevent interactions that may be attributed to involuntary tremors.

III. Further Comments and/or Embodiments

Some embodiments of the present invention recognize the following facts, potential problems and/or potential areas for improvement with respect to the current state of the art: (i) while interacting with digital contents, like selecting menus, typing text etc., the relative movement of user's finger and interaction point should be stable so that user can select the required content easily; (ii) for Parkinson's disease patients and others with hand tremors, the relative position will keep on changing, and thus the user will not be able to type or select menu properly; (iii) if there is any hand tremor then it will be difficult for the user to interact with digital content; (iv) there is opportunity for a method and system by which Parkinson's disease patients and others with hand tremors can interact with digital content without much difficulty; (v) in different cognitive states of typical people, specific nervous system disorders can affect movement of the fingers; (vi) for nervous system disorders, symptoms start gradually, sometimes starting with a barely noticeable tremor in just one hand; (vii) tremors are common, but the disorder also commonly causes stiffness or slowing of movement; (viii) at the same time, various cognitive states, like anxiety or freight can introduce a tremor in the hand, and at the same time, hand tremor can happen because of fatigue in hand; (ix) some known causes of hand tremors include: (a) multiple sclerosis, (b) strokes, (c) traumatic brain injuries, (d) Parkinson's disease, (e) essential tremor, (f) dystonic tremor, (g) depression, (h) anxiety/panic, (i) post-traumatic stress disorder, (j) inherited ataxia, (k) fragile X syndrome, (l) mercury poisoning, (m) hyperthyroidism, (n) liver/kidney failure, and (o) certain medications; (x) head mounted augmented reality devices are also getting very popular; (xi) in this case, digital contents are projected onto the retina, so that user can visualize the digital content in the surrounding in different depth; and (xii) there exists a need for a method and system by which users can interact with digital content when hand tremors are detected.

Some embodiments of the present invention may include one, or more, of the following operations, features, characteristics and/or advantages: (i) a method and system by which Parkinson's disease patient's 3D hand movement pattern is historically learnt along with their level of comfort while interacting with digital content; (ii) accordingly AR glass will dynamically project the digital content in different depth aligned with finger movement pattern, so that the said user can comfortably interact with digital contents; (iii) Based on predicted types and degree of hand tremor, the proposed system will be predicting next hand movement of finger and accordingly digital content will be arranged; (iv) Parkinson's disease is a progressive nervous system disorder that affects movement; (v) symptoms start gradually, sometimes starting with a barely noticeable tremor in just one hand; (vi) tremors are common, but the disorder also commonly causes stiffness or slowing of movement; (vii) in the early stages of Parkinson's disease, the patient's face may show little or no expression; (viii) arms may not swing when walking; (ix) speech may become soft or slurred; (x) Parkinson's disease symptoms worsen as the condition progresses over time; (xi) Head mounted Augmented reality devices are gaining popularity; and (xii) in this case, digital contents are projected on the retina so that the user can visualize the digital content in their surroundings at different depths.

Some embodiments of the present invention may include one, or more, of the following operations, features, characteristics and/or advantages: (i) using fingernail sensors, a Parkinson's disease patient's finger movement pattern (like relative position, depth of fingertips changes along shaking pattern of hand) will be historically learnt; (ii) accordingly the digital contents will be aligned around the fingertips of the user, so that user can interact with the digital contents comfortably; (iii) the relative position and depth of each fingertips along with shaking pattern of fingers and movement pattern of the hand will be predicted in different contextual situations and accordingly identify the position of different contents for creation around the fingertips; (iv) thus the AR glasses or HMD will project the digital contents to the retina so that user can interact with the digital contents; (v) using historical learning, identify the sequence of finger movements of the patient and accordingly align the sequence of contents around the sequence of fingertip movement of the user, so that appropriate digital content can be placed around the fingertip of the user; (vi) by analyzing the fingernail feed of the user, track improvement or deterioration rate of the user in terms of shaking of fingers or hand, and accordingly, dynamically adjust the positioning the digital content aligned with 3D position of the fingertips; (vii) consider additional movement based on the surrounding context; (viii) for example, the Parkinson's disease patient is travelling in a vehicle, or walking etc.; (ix) these movements will also create additional movement (in the fingers), and the AR glasses or HMD will adjust the digital content around the fingertip of the user; (x) using historical learning, identify which fingers are most active to perform different activities, and accordingly the digital contents will be aligned with those active fingers, so that user can comfortably perform interaction with digital contents; (xi) track hand movement behavior of any user while interacting with digital content (for example, the user is identified as confused on selecting desired content, not sure which one to select); (xii) accordingly digital content will dynamically be aligned with finger position; (xiii) track if the user has selected the content as per the proper sequence of content navigation (for example, after filling a web page the user has to select submit button); (xiv) accordingly the next finger movement will be predicted and the appropriate navigation sequence will be repositioned; (xv) dimension of the content can also be altered; and (xvi) based on historical learning that includes the hand shaking pattern, health condition, cognitive state, predict the next finger movement, and accordingly when any content is displayed, predict where the user's finger will be moving.

Some embodiments of the present invention may include one, or more, of the following operations, features, characteristics and/or advantages: (i) predicting tendency of hand tremor based on various contextual situation and considering the predicted tendency of hand tremor and align the digital content with AR glass; (ii) users 3D hand movement will historically be learnt and aligned with level of comfort while interacting with digital content and accordingly AR glass will dynamically be placing the digital content in different depth and positions aligned with predicted finger movement direction and pattern, so that the said user can comfortably interact with digital contents; (iii) using Fingernail sensors, a user's finger movement pattern (like relative position, depth of fingertips changes along shaking pattern of hand) will historical be learnt, and accordingly the digital contents will be aligning around the fingertips of the user, so that user can interact with the digital contents comfortably; (iv) in this case the digital content will be tracking false interaction pattern with different content and will be predicting if the user is having any tendency of hand tremor; (v) using historical learning on user's hand tremor reason and pattern will be predicted, and based on how content is navigated, predict next finger movement pattern and direction, and accordingly AR glasses/HMD will proactively create digital content in front of the fingertip in a proactive manner; and (vi) predicting tendency of hand tremor based on historical learning and finger nail sensors and predicting how mid-air AR object can be created aligned with predicted hand movement.

Figure 8:
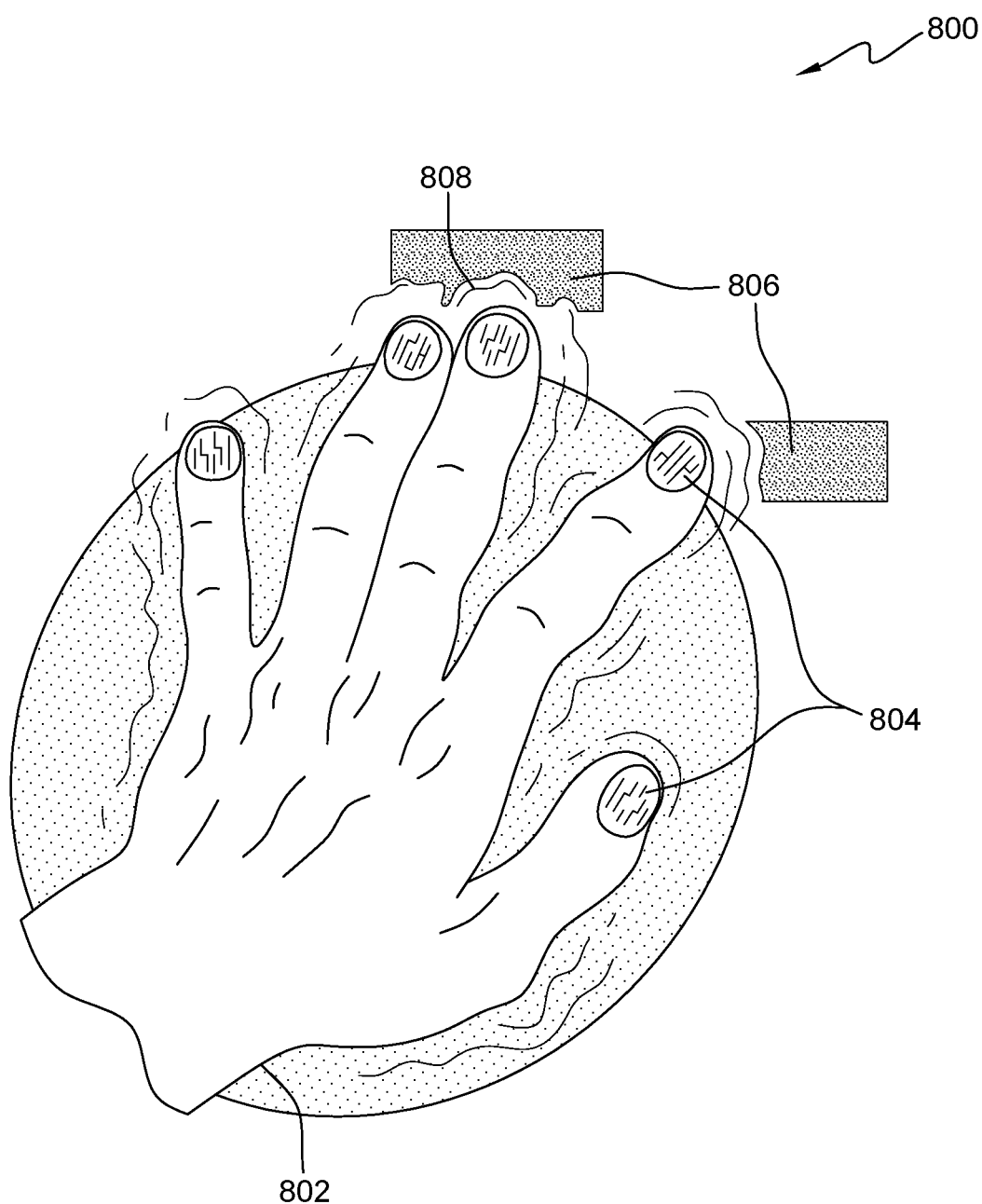
FIG. 8 is a block diagram view of a second embodiment system according to the present invention.

Referring to FIG. 8, diagram 800 shows a second embodiment system with fingernail circuits 804 placed on fingernails of hand 802. An AR device (not shown) projects interactive digital contents 806 into the view of a user wearing the AR device and fingernail circuits 804. Fingernail circuits 804 identify the appropriate depth of the user's fingers based on their historical tremor pattern and present involuntary finger movements 808 and projects interactive digital contents 806 at the appropriate depth and horizontal/vertical positions.

Some embodiments of the present invention may include one, or more, of the following operations, features, characteristics and/or advantages: (i) fingernail circuits are printed on each fingernail of the users who have hand tremor history for various reasons mentioned above; (ii) fingernail circuits have movement and proximity sensors printed so that relative movement of the fingers can be identified individually; (iii) based on the feed from each fingernail circuit, the 3D position of each and every finger is identified and will also determine relative movement of the fingers; (iv) each fingernail circuit is identified uniquely and will historically track the movement pattern of the fingers; (v) the user can also wear wearable devices, so the wearable device feed can also track and identify the movement of their hands; (vi) while tracking the finger movement pattern, also track any other mobility pattern of the user, like walking, travelling with vehicle etc.; (vii) historical data is captured from the fingernail circuits, wearable devices, of the user etc.; (viii) the fingernail and wearable devices of the user will identify: (a) the pattern of shaking of the fingers, (b) relative position of the fingers during shaking, (c) relative depth of each of the fingertips, (d) speed of movement of the fingers with respect to the shaking, and (e) sequence of shaking of the fingers, etc.; (ix) based on historical learning about the above information in different contextual situations, create a knowledge corpus about the finger movement pattern of any user having hand tremor history for any reason; (x) using any existing method content will be predicted, like while typing any content keyword is predicted and displaying in the screen; (xi) also consider the contextual situation of typing or digital content interaction need of the user; (xii) user's input for digital content interaction can be identified based on user's contextual situation, historical content consumption, or any writing need, etc.; (xiii) while writing any text, use any exiting method to predict the keywords, etc.; (xiv) an AR device will determine the user's finger position and determine the relative position of the fingers in different depth; (xv) sequence of finger movement is also tracked based on the historical learning; (xvi) sequence of content interaction is also identified, such as sequence of keywords while typing, etc.; (xvii) the AR device will also determine the real-time position of each of the fingertip of the user; (xviii) the AR device will also identify which fingertips are active and perform better interaction with digital contents; (xix) the AR device will also determine the depth of each of the fingertip of the user; (xx) using historical learning, predict the shaking pattern of the fingers; (xxi) the digital contents are aligned around each fingertip of the user, and this alignment is done based on the shaking pattern of the fingers; and (xxii) the alignment of the digital content is aligned with the shaking pattern of the fingers so that user can interact with the digital content in a comfortable manner.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

In an Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, and application-specific integrated circuit (ASIC) based devices.

What is claimed is:

1. A computer-implemented method (CIM) for use with an augmented reality (AR) device, the CIM comprising:
    receiving a historical hand tremor data set corresponding to a user;
    determining a hand tremor pattern based, at least in part, on the historical hand tremor data set;
    displaying an augmented reality user interface on the AR device worn by the user;
    determining a potential user interface interaction between at least one hand of the user and a user interface element of the augmented reality user interface; and
    modifying the augmented reality user interface based, at least in part, on the hand tremor pattern, including modifying the user interface element based on hand tremor amplitude and synchronized to frequency measurements indicated in the hand tremor pattern.

2. The CIM of claim 1, wherein determining the potential user interface interaction further comprises:
    comparing present movements of the at least one hand of the user to the hand tremor pattern; and
    filtering at least some movements of the present movements corresponding to an involuntary hand tremor based, at least in part on the comparison to isolate voluntary movements from involuntary movements.

3. The CIM of claim 1, wherein modifying the augmented reality user interface further comprises:
    modifying positional coordinates of the user interface element, with the modifications to the positional coordinates corresponding to involuntary movements associated with a hand tremor; and
    displaying the user interface element with the modified positional coordinates.

4. The CIM of claim 1, wherein modifying the augmented reality user interface further comprises:
    enlarging the user interface element based, at least in part, on the hand tremor pattern.

5. The CIM of claim 4, wherein enlarging the user interface element further comprises:
    for the user interface element, expanding the user interface element along a horizontal axis, with the degree of expansion based, at least in part, on the hand tremor pattern; and
    for the user interface element, expanding the user interface element along a vertical axis, with the degree of expansion based, at least in part, on the hand tremor pattern.

6. The CIM of claim 1, wherein the historical hand tremor data set is generated from historical fingertip positional data measured by one or more fingernail circuits printed on one or more fingernails of the user.

7. The CIM of claim 1, wherein the potential user interface interaction is a gesture-based input received from a camera component of the AR device.

8. A computer program product (CPP) for use with an augmented reality (AR) device, the CPP comprising:
    a machine readable storage device; and
    computer code stored on the machine readable storage device, with the computer code including instructions for causing a processor(s) set to perform operations including the following:
        receiving a historical hand tremor data set corresponding to a user,
        determining a hand tremor pattern based, at least in part, on the historical hand tremor data set,
        displaying an augmented reality user interface on the AR device worn by the user,
        determining a potential user interface interaction between at least one hand of the user and a user interface element of the augmented reality user interface, and
        modifying the augmented reality user interface based, at least in part, on the hand tremor pattern, including modifying the user interface element based on hand tremor amplitude and synchronized to frequency measurements indicated in the hand tremor pattern.

9. The CPP of claim 8, wherein determining the potential user interface interaction further includes instructions for causing the processor(s) set to perform the following operations:
    comparing present movements of the at least one hand of the user to the hand tremor pattern; and
    filtering at least some movements of the present movements corresponding to an involuntary hand tremor based, at least in part on the comparison to isolate voluntary movements from involuntary movements.

10. The CPP of claim 8, wherein modifying the augmented reality user interface further includes instructions for causing the processor(s) set to perform the following operations:
    modifying positional coordinates of the user interface element, with the modifications to the positional coordinates corresponding to involuntary movements associated with a hand tremor; and
    displaying the user interface element with the modified positional coordinates.

11. The CPP of claim 8, wherein modifying the augmented reality user interface further includes instructions for causing the processor(s) set to perform the following operations:
    enlarging the user interface element based, at least in part, on the hand tremor pattern.

12. The CPP of claim 11, wherein enlarging the user interface element further includes instructions for causing the processor(s) set to perform the following operations:

for the user interface element, expanding the user interface element along a horizontal axis, with the degree of expansion based, at least in part, on the hand tremor pattern; and for the user interface element, expanding the user interface element along a vertical axis, with the degree of expansion based, at least in part, on the hand tremor pattern.

13. The CPP of claim 8, wherein the historical hand tremor data set is generated from historical fingertip positional data measured by one or more fingernail circuits printed on one or more fingernails of the user.

14. The CPP of claim 8, wherein the potential user interface interaction is a gesture-based input received from a camera component of the AR device.

15. A computer system (CS) for use with an augmented reality (AR) device, the CS comprising:

a processor(s) set;

a machine readable storage device; and computer code stored on the machine readable storage device, with the computer code including instructions for causing the processor(s) set to perform operations including the following:

receiving a historical hand tremor data set corresponding to a user, determining a hand tremor pattern based, at least in part, on the historical hand tremor data set, displaying an augmented reality user interface on the AR device worn by the user, determining a potential user interface interaction between at least one hand of the user and a user interface element of the augmented reality user interface, and modifying the augmented reality user interface based, at least in part, on the hand tremor pattern, including modifying the user interface element based on hand tremor amplitude and synchronized to frequency measurements indicated in the hand tremor pattern.

16. The CS of claim 15, wherein determining the potential user interface interaction further includes instructions for causing the processor(s) set to perform the following operations:

comparing present movements of the at least one hand of the user to the hand tremor pattern; and filtering at least some movements of the present movements corresponding to an involuntary hand tremor based, at least in part on the comparison to isolate voluntary movements from involuntary movements.

17. The CS of claim 15, wherein modifying the augmented reality user interface further includes instructions for causing the processor(s) set to perform the following operations:

modifying positional coordinates of the user interface element, with the modifications to the positional coordinates corresponding to involuntary movements associated with a hand tremor; and displaying the user interface element with the modified positional coordinates.

18. The CS of claim 15, wherein modifying the augmented reality user interface further includes instructions for causing the processor(s) set to perform the following operations:

enlarging the user interface element based, at least in part, on the hand tremor pattern.

19. The CS of claim 18, wherein enlarging the user interface element further includes instructions for causing the processor(s) set to perform the following operations:

for the user interface element, expanding the user interface element along a horizontal axis, with the degree of expansion based, at least in part, on the hand tremor pattern; and for the user interface element, expanding the user interface element along a vertical axis, with the degree of expansion based, at least in part, on the hand tremor pattern.

20. The CS of claim 15, wherein the historical hand tremor data set is generated from historical fingertip positional data measured by one or more fingernail circuits printed on one or more fingernails of the user.

* * * * *